United States Patent [19]

Rai

[11] Patent Number: 4,995,878
[45] Date of Patent: Feb. 26, 1991

[54] METHOD FOR DESCENDING VENOGRAPHY

[76] Inventor: Dinker B. Rai, 230-20 53rd Ave., Bayside, N.Y. 11364

[21] Appl. No.: 219,140

[22] Filed: Jul. 15, 1988

[51] Int. Cl.$^5$ ............................................. A61M 25/01
[52] U.S. Cl. ..................................... 606/194; 604/96; 604/170; 128/657
[58] Field of Search ........................... 604/93, 95–104, 604/164, 170, 280–284, 52–53, 158; 128/341, 343–344, 656–658, 772, 691–692, 672–673; 606/192, 194–195

[56] References Cited

U.S. PATENT DOCUMENTS

| | | | |
|---|---|---|---|
| 4,033,331 | 7/1977 | Guss et al. | 604/281 X |
| 4,299,226 | 11/1981 | Banka | 128/657 LX |
| 4,468,224 | 8/1984 | Enzmann et al. | 604/164 X |
| 4,509,945 | 4/1985 | Kramann et al. | 128/657 X |
| 4,650,472 | 3/1987 | Bates | 604/170 X |
| 4,662,366 | 5/1987 | Tari | 128/878 X |
| 4,682,607 | 7/1987 | Vaillancourt et al. | 604/95 X |
| 4,747,840 | 5/1988 | Ladika et al. | 604/280 X |
| 4,762,129 | 8/1988 | Bonzel | 604/96 X |
| 4,771,777 | 9/1988 | Horzewski et al. | 128/344 |
| 4,782,834 | 11/1988 | Maguire et al. | 604/280 X |
| 4,784,639 | 11/1988 | Patel | 604/280 X |
| 4,790,331 | 12/1988 | Okada et al. | 604/53 X |

Primary Examiner—Angela D. Sykes

[57] ABSTRACT

A method and the apparatus for retrograde catheterization of the venous tree of the lower extremity by introducing the catheter percutaneously through one of superficial veins of the upper extremity (forearm) of the human body and advancing the catheter in a retrograde fashion between the valve cusps in a patient awake and kept in erect posture enabling to perform descending venography to evaluate all types of chronic venous insufficiency. An angiocatheter is introduced in a superficial vein in the forearm and a guidewire having a 'J' tip with movable core is inserted into said angiocatheter and advanced within the superficial vein in forearm. While leaving the guidewire in place angiocatheter is removed and replaced with a vessel dilator and site of entry is dilated around the guidewire. Then the vessel dilator is removed and an elongated catheter having diameter sufficiently small enough to pass unobstructed through the superficial vein is introduced into the peripheral vein of the forearm. The guidewire is introduced from the superficial vein through superior vena cava, right atrium of heart, inferior vena cava and into the desired iliac vein. Along the guidewire catheter is advanced. Then onwards catheter is advanced between the cusps of the valve encountered using the balloon inflation and deflation method described in the art to a desired level into the femoral veins in the thigh or beyond if necessary. Thus the proximal and distal valves in the venous tree of the lower extremity is examined by performing descending venography by injecting X-ray contrasting fluid through the catheter or if the venous insufficiency is due to venous obstructive disease due to venous blood clots it could be retrieved and removed at a desired proximal site in the venous tree.

9 Claims, 4 Drawing Sheets

METHOD FOR DESCENDING VENOGRAPHY

BACKGROUND OF THE INVENTION

This invention relates to a method for evaluating venous disease in the lower extremities of the human body.

More specifically, this invention relates to a method for evaluating venous insufficiency, or lack of blood flow through veins in the body in the lower extremities, due to the incompetence of valvular functions or obstructions in the veins.

The evaluation of venous disease in the lower extremities of the body has become more important due to new surgical techniques that have developed for correcting the valvular insufficiency of the veins. Venous insufficiency, or the lack of blood flow in the veins of the lower extremities of the body, typically causes varicose veins, edema, skin pigmentation, claudication, venous ulcers, as well as a great deal of discomfort to the patient. There have been some techniques proposed for the non-invasive examination of venous insufficiency, such as using bi-directional Doppler ultrasonics and radionuclide techniques to study the motion of the blood through the veins of the lower extremities of the body. In one technique, a radioisotope, such as Renografin-60, is slowly injected into the veins of the patient while under fluoroscopic observation, and spot images are obtained of the veins in the leg and thigh.

In order to maintain the proper flow of blood through the veins of the lower extremities of the body, the femoral vein, which is an extension of the inferior vena cava from the heart, contains one or more valves which prevent the blood from descending or reversing flow in the vein during the pumping suction action of the heart. When the valves become damaged, there is an insufficiency of blood flow in the lower extremities, which causes a great deal of discomfort to the patient.

Accordingly, the present invention provides an invasive, non-surgical technique of evaluating venous insufficiency in the deep veins of the lower extremities, that is, the legs and thighs, so that proper surgical techniques can be applied.

In the method of the present invention, which is known as pericarpal percutaneous catheterization, any one of the available veins around the wrist or the distal one-third of the forearm is used for percutaneous catheterization. With this technique, an angiocatheter is introduced into the vein of the arm, which is later substituted for a longer venous catheter with a balloon at the tip and curved end, so that the catheter can be guided through the right atrium of the heart and into the inferior vena cava, and then advanced into the desired iliac vein and placed at the level of the inferior ramus of ischium. An X-ray contrasting material is then injected into the catheter and the competency of the valves and patency of the veins are studied under fluoroscopy. If the valves are incompetent, or not preventing the back-flow of the blood in the veins of the leg and thigh, the contrasting material viewed under fluoroscopy will show that the flow is retrograde. With this proper diagnosis, a surgically invasive or non-invasive technique can then be applied to correct the venous insufficiency.

This method of the invention is called the upper extremity approach.

In the prior art there is also other approaches which have a number of disadvantages for the patient. There is the transbrachial catheterization approach wherein a venous cut down is made just above the medial epicondyle of the humerus in the upper arm. The transbreachial approach has many disadvantages since it requires the insertion of a catheter into deep veins which therefore requires surgery and causes a great deal of discomfort to the patient.

In the prior art there is also the transcervical approach wherein the internal jugular or subclavian vein receives the guide wire and venous catheter for performing the examination. This has the disadvantage of being a blind approach with danger and risk of causing injury to the lungs including puncturing the lungs with the guide wire causing an air leak in the chest. There is also a great deal of bleeding that occurs in the transcervical approach.

Another conventional approach for venous examination is the transgroin approach which is also a blind procedure. Whether the transgroin approach is contralateral or ipsilateral this approach runs a high risk of injuring the arteries and producing blood clots in the veins.

The present invention provides many advantages over the conventional approaches by utilizing a superficial vein located around the wrist or in the forearm where is little or no danger of creating blood clots, puncturing the lungs or requiring any deep invasive surgery. The upper extremity approach of the present invention according to the invention was made possible by significantly reducing the diameter of the catheter so that it would experience little or no obstruction as it advanced through the superficial vein and ultimately through the femoral vein in the groin. More over, the invention utilizes a catheter and guide wire that have been greatly elongated over conventional catheters and guide wires in order to facilitate the longer distances in which the catheter and guide wire have to travel before they reach the distal part of the femoral vein.

Accordingly, it is an object of the present invention to provide a method for diagnosing all types of chronic venous insufficiency.

It is another object, according to the present invention, to provide an improved method for diagnosing chronic venous insufficiency using interchangeable catheters to more precisely locate, evaluate and determine the amount of insufficiency of the veins of the lower extremities of the body.

It is another object, according to the present invention, to diagnose venous insufficiency due to venous thrombosis and to provide a method for retrograde catheterization of the venous tree to retrieve venous blood clots.

Other objects and features of the present invention will become apparent from the following detailed description considered in connection with the accompanying drawings which disclose the embodiments and method of the present invention.

BRIEF DESCRIPTION OF THE DRAWINGS

In the drawings, wherein similar reference characters denote similar elements throughout the several views.

DESCRIPTION OF THE PREFERRED EMBODIMENTS

Figure 1:
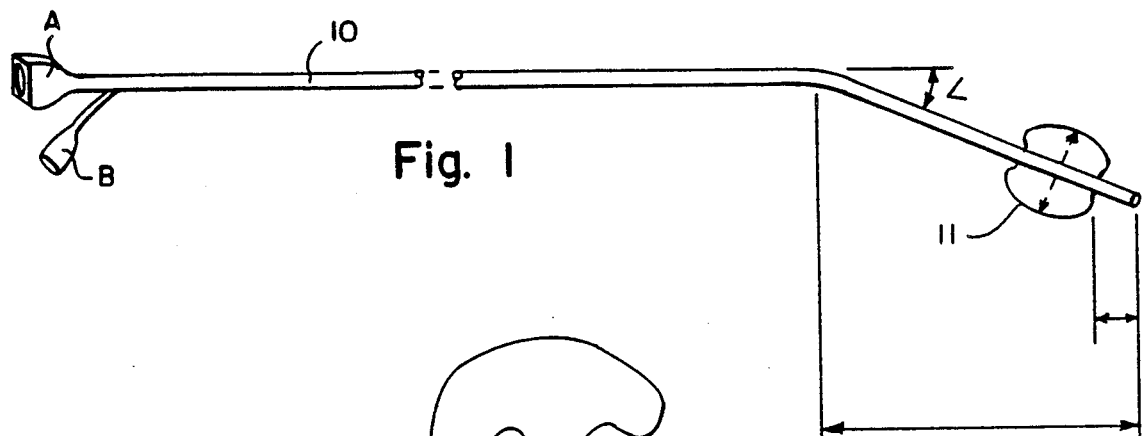
FIG. 1 is a plan view of a pericarpal percutaneous venus catheter used in the final stages of the method of the present invention.

There is shown a preferred descending venogram catheter for use in a superficial vein in the forearm or wrist of the patient that is preferably 140 cm in length and having a diameter of French size 6. This catheter is preferably bent at an angle of approximately 15° within the last 5 cm of its distal end. The catheter is also preferably provided with a balloon located within a half a centimeter of its distal end which can be inflated to a diameter preferably of 1.5 cm. The catheter 10 of FIG. 1 is preferably provided with 2 openings A and B at its proximal end which are commonly referred to as lumens. Opening A is a multi purpose opening which will fit in injection syringes or IV tubes to inject contrasting dye into the veins of the patient. This lumen can also receive and accommodate a guide wire prefereably having a diameter of 0.028". Lumen B is a separate lumen from lumen A and is used to inflate a balloon 11 at the distal end of catheter 10 by using a syringe (not shown). In order to perform an upper extremity approach for venography the following equipment should be assembled and used:

1. A No. 18 gauge angiocatheter;
2. A 5 cc syringe;
3. A 6.3 French venous dilator;
4. A 165 cm. long 0.028" diameter guide wire 12 with 1.5 mm "J" tip 13 with movable core; and
5. The 140 cm long No. 6 French venous catheter 10 with balloon at the tip and curved end as shown in FIG. 1

Figure 2:
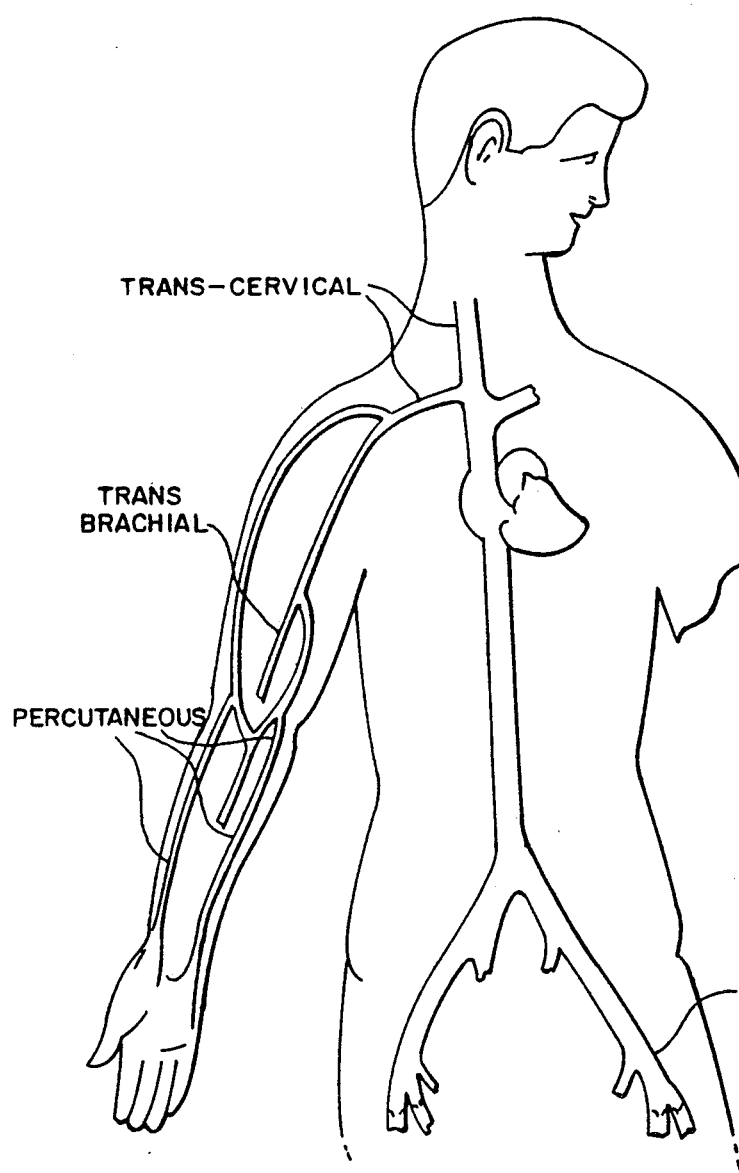
FIG. 2 is a plan view, partly in cross-section of the veins of the body showing different sites for catheterization.
Figure 4:
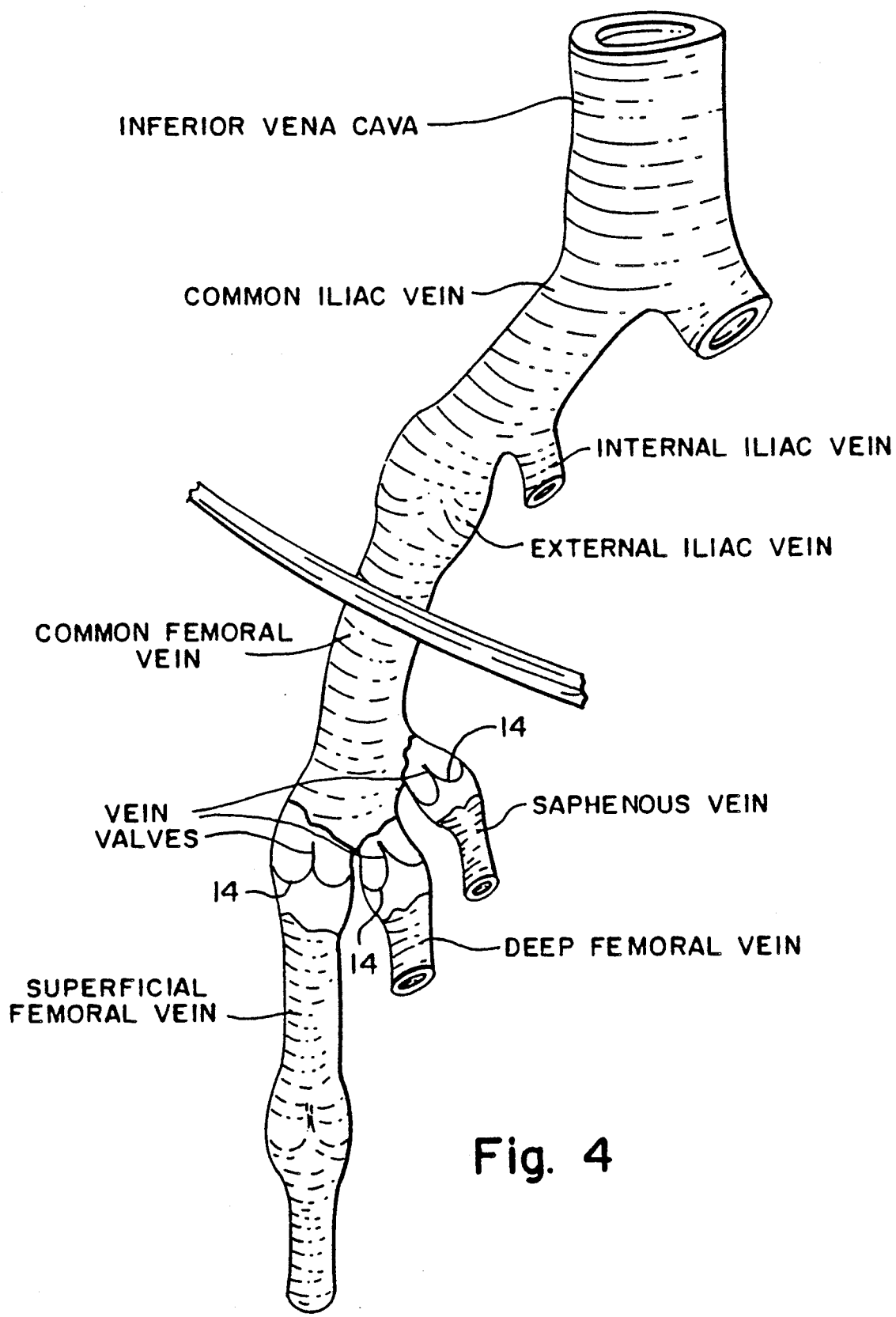
FIG. 4 shows the common location of the valves in the lower extremity venous system.

Using the above-described equipment, it is possible to perform a pericarpal percutaneous catheterization. A superficial vein around the wrist or in the forearm is selected as shown in FIG. 2. The vein should be of a reasonable size and nontortuous. The forearm and wrist of the patient are prepped and draped. A tourniquet is then applied to the proximal part. Under local anethesia, a No. 18 gauge angiocatheter is introduced into the vein. The metal stylet is then removed and guide wire 12 with "J" tip 13 is introduced into the vein through the angiocatheter and carefully advanced for a distance of 20 cm. Then the angiocatheter is removed and a small skin incision is made to introduce the venous dilator. A dilator is introduced through the guide wire and the opening is dilated. The venous dilator is removed and main elongated catheter 10 of FIG. 1 is introduced. Catheter 10 is advanced along the guide wire. The passage of guide wire 12 from the subclavian vein into the inferior vena cava through the right atrium of the heart is always performed under fluoroscopy. More than 90% of the time, catheter 10 normally slips into the inferior vena cava. Occasionally, however, it can enter the right ventricle. When it does, guide wire 12 begins to oscillate and curves to the left. Under such circumstances, the guide wire is pulled back into the atrium and manipulated into the inferior vena cava. The progression of guide wire 12 must always be smooth and without resistance. If resistance is encountered at any place during the advancement of the guide wire, it is removed with the catheter in place, and a venogram is performed by injecting a contrast fluid to delineate the anatomy. A balloon inflation would be useful to prevent retrograde flow and wastage of the dye. Then catheter 10 is advanced into the desired external iliac vein, and placed at the level of inferior ramus of ischium. At this stage, the X-ray table is tilted to a 60° upright position and the contrast fluid is injected using either hand injection or medrad pressure injection at 300–500 ASI. The competency of the valves 14 and the patency of the veins are studied under fluoroscopy. When the valves are incompetent, the contrast fluid flows retrograde into the veins of thigh and leg. Films are taken of the pelvis, thigh and calf area. FIG. 4 is a detailed view of the inferior vena cava, and shows the common location of the valves in the lower extremity of the venous system, which are typically examined for venous insufficiency using noninvasive examination technics.

In some patients who manifest the signs and symptoms of chronic venous insufficiency, the proximal valves in the common femoral area may be partially or even totally competent. Hence, the contrast fluid may fail to reach the veins of the lower thigh and leg. In these patients, the diagnosis and evaluation becomes incomplete. Under the circumstances, the selective catheterization of the superficial femoral vein is recommended to evaluate valves of the distal femoral and popliteal vein segment. This should be done without causing damage to the proximal valves.

Figure 3A:
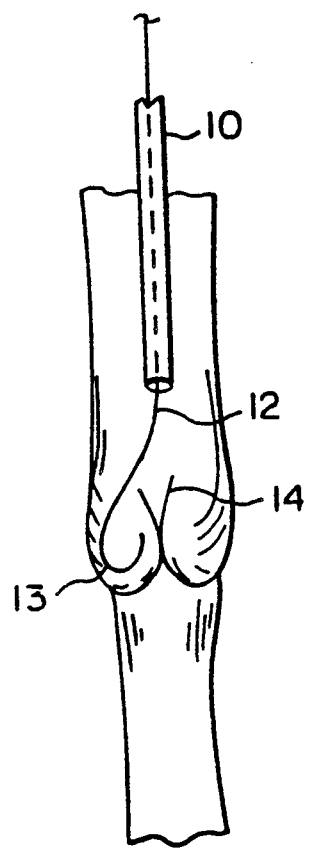
FIG. 3a and 3b are enlarged views of the valves located in the veins of the lower extremities and the use of an inflated balloon to separate the cusps of the valves to permit advancement of a guide wire between the valves.
Figure 3B:
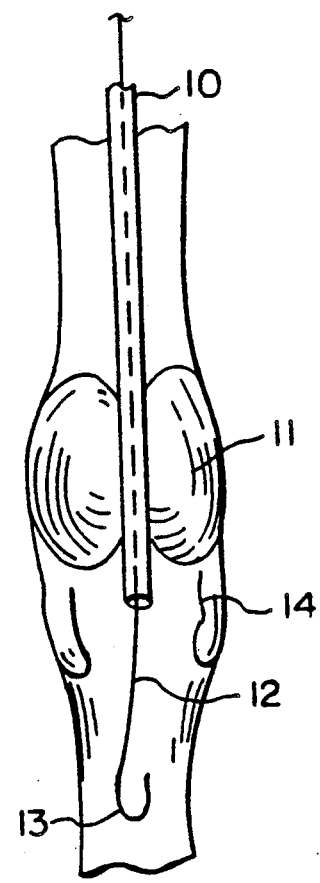
Figure 5:
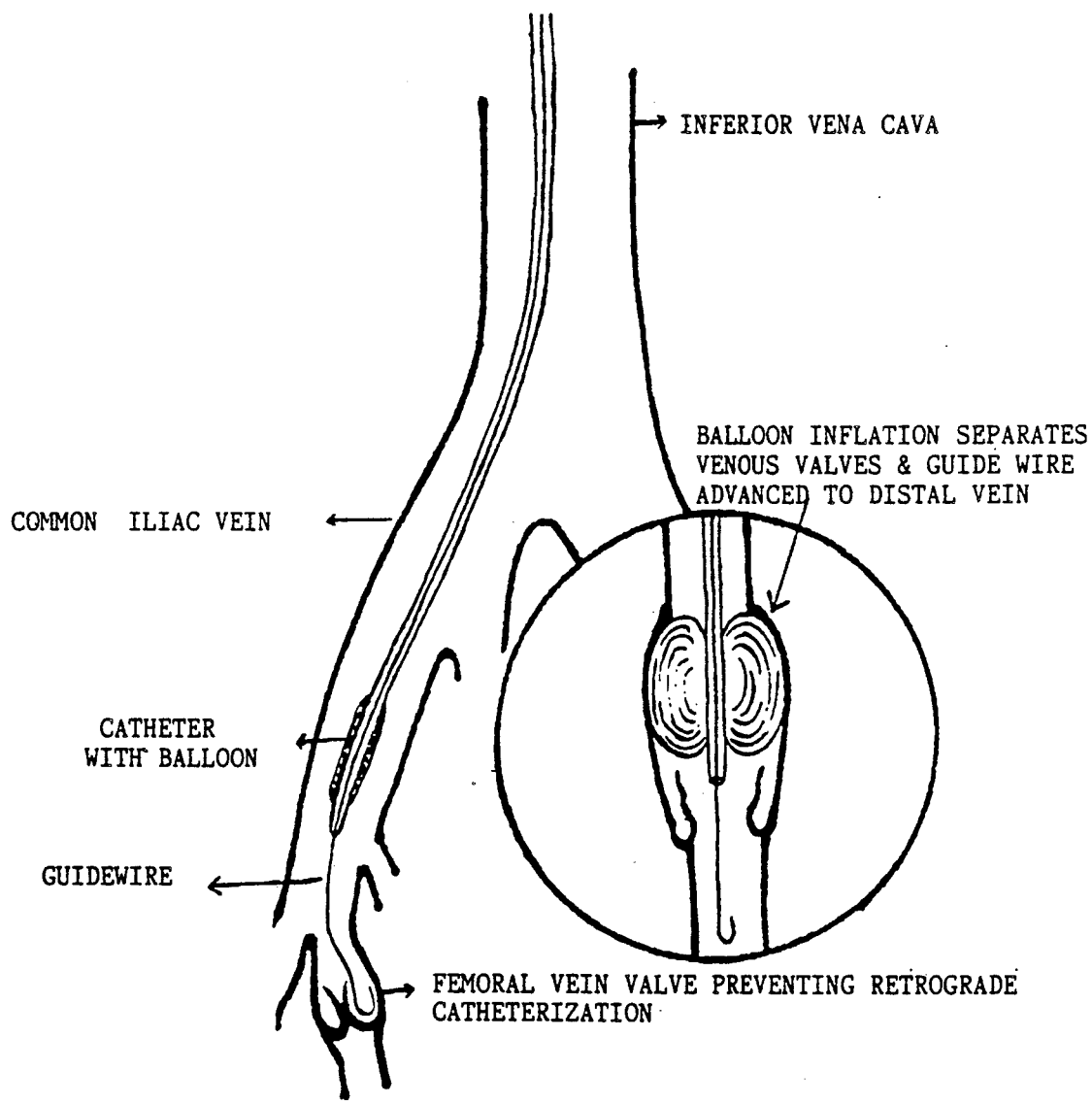
FIG. 5 shows the femoral vein valves preventing retrograde advancement of the catheter and the guidewire. Figure enclosed within the circle is the enlarged view of the technique of separating the valves by inflating the balloon and then passing the guidewire between the valve cups. Once the guidewire is passed, balloon is deflated and the catheter is advanced along the guidewire beyond the valves in a retrograde manner. Thereafter each valve encountered is passed in the similar manner.

Two methods are recommended as follows:
a. The patient is asked to take deep expiration. During expiration, femoral vein valves 14 open widely and during this time, advance the tip of the guide wire gently between valves 14, and then advance catheter 10.
b. Valve 14 is then closed (FIG. 3a), and balloon 11 of catheter 10 is gently inflated to dilate the vein segment. This separates the valve cusps widely apart (FIG. 3b). Guide wire 12 is then advanced between the cusps to the distal vein, and balloon is deflated and then catheter 10 is subsequently advanced (see FIG. 5). Balloon inflation 11 is a self-protecting mechanism to prevent damage to the veins. In spite of that, it is recommended that there be a cautious inflation of the balloon. Using the same technique catheter is advanced beyond subsequent vein valves in a retrograde fashion to a desired level. At each level competency of vein valves tested by injecting X-ray contrast fluid. If the venous insufficiency is due to obstruction of the vein due to blood clot then the guidewire is left at the desired place in the vein and catheter is withdrawn by inflating the balloon, thereby blood clot is dislodged, retrieved and removed at a desired proximal level.

The peri-carpal percutaneous approach and method of the present invention overcomes many of the disadvantages of the other approaches and results in less discomfort for the patient.

While only several embodiments and examples of the present invention have been described, it is obvious that many changes and modifications may be made thereunto, without departing from the spirit and scope of the invention.

What is claimed is:

1. A method for the evaluation of all types of chronic venous insufficiency of the lower extremities of the human body comprising the steps of:

introducing an angiocatheter into a superficial vein in the forearm of the body;

inserting a guide wire having a "J"-shaped tip into said angiocatheter and advancing said guide wire within the superficial vein of the forearm;

removing said angiocatheter from the superficial vein in the forearm while leaving the guide wire in place in the vein;

dilating the opening of the superficial vein around said guide wire;

introducing an elongated catheter having a diameter sufficiently small to pass unobstructed through the superficial vein of the forearm, and having a length sufficient to reach the distal thigh;

allowing the guide wire to be introduced from the superficial vein through the heart into the inferior vena cava and into the femoral vein in the groin;

simultaneously advancing said elongated catheter on said guide wire into said femoral vein in the groin of the body to examine the proximal valves of the femoral vein;

injecting an X-ray contrast fluid into said elongated catheter; and examining and evaluating competency of said valves in the femoral vein under fluoroscopy.

2. The method as recited in claim 1, wherein said step of advancing additionally comprises inflating a balloon at the distal end of said elongated catheter thereby separating the cusps of the proximal valve being examined, and advancing the guide wire between the cusps beyond the valve.

3. The method as recited in claim 2, additionally comprising deflating said balloon and advancing said elongated catheter along the guide wire beyond the proximal valve to a distal valve.

4. The method as recited in claim 3, wherein said elongated catheter has at least 2 lumens, one to receive said guide wire and contrast fluid and a second lumen for the inflation of said balloon.

5. The method as recited in claim 4, wherein said balloon is located at the distal end of said catheter approximately 0.5 cm from the end.

6. The method as recited in claim 5, wherein said balloon can be inflated to a diameter of 1.5 cm.

7. The method as recited in claim 1, wherein said elongated catheter is 140 cm in length and has a diameter of number 6 French.

8. The method as recited in claim 7, wherein the last 5 cm of the distal end of said catheter is bent at an angle of approximately 15°.

9. The method as recited in claim 1, wherein said guide wire is 165 cm in length and has a diameter of 0.028".

* * * * *